United States Patent [19]

Vogt et al.

[11] 4,271,008

[45] Jun. 2, 1981

[54] PRODUCTION OF ETHYLENE

[75] Inventors: Wilhelm Vogt, Hürth; Hermann Glaser, Erftstadt, both of Fed. Rep. of Germany

[73] Assignee: Hoechst Aktiengesellschaft, Fed. Rep. of Germany

[21] Appl. No.: 98,609

[22] Filed: Nov. 29, 1979

[30] Foreign Application Priority Data

Dec. 4, 1978 [DE] Fed. Rep. of Germany ....... 2852314

[51] Int. Cl.³ .......................... C10C 9/16; C07C 4/04; C07C 11/04
[52] U.S. Cl. .................................. 208/48 R; 208/129; 208/130; 585/650; 585/652; 585/950
[58] Field of Search ............. 208/48 R, 950, 129–130; 585/651, 652, 650

[56] References Cited

U.S. PATENT DOCUMENTS

| 2,621,216 | 12/1952 | White | 585/654 |
| 3,827,967 | 8/1974 | Nap et al. | 208/48 R |

FOREIGN PATENT DOCUMENTS 364043  5/1931  United Kingdom ...................... 585/651

Primary Examiner—Delbert E. Gantz
Assistant Examiner—G. E. Schmitkons
Attorney, Agent, or Firm—Connolly and Hutz

[57] ABSTRACT

The invention relates to a process for making ethylene by subjecting a gas mixture containing hydrocarbons, hydrogen, carbon monoxide, carbon dioxide and steam to a hydropyrolysis reaction. More particularly, the gas mixture is heated to temperatures higher than 800° C. inside a reaction zone having metal walls. The walls contain aluminum and/or copper in at least their surface portions.

5 Claims, No Drawings

PRODUCTION OF ETHYLENE

This invention relates to a process for making ethylene by subjecting a gas mixture containing hydrocarbons, hydrogen, carbon monoxide, carbon dioxide and steam to a hydropyrolysis reaction.

A process for making ethane and/or ethylene has been described, wherein a reaction mixture consisting of hydrocarbons, carbon monoxide, carbon dioxide, water and hydrogen (the mixture being obtained by reacting hydrogen with carbon monoxide in a molar ratio of 1:1 to 5:1 in contact with a Fischer-Tropsch catalyst containing iron, cobalt, nickel or ruthenium) is pyrolyzed inside a hydropyrolyzing zone at a temperature of 600° to 900° C., under a pressure of at least 5 bars and over a period of 0.1 to 60 seconds, and the resulting gas mixture issuing from the hydropyrolyzing zone is treated so as to separate $C_2$-hydrocarbons therefrom. For effecting the hydropyrolysis reaction just described, use can be made of a reactor which has a heat-resistant steel cylinder placed therein, which faces and comes into contact with the reaction mixture. As to those mixtures which are obtained by the catalytic reduction of carbon monoxide with hydrogen by a process, such as described in British Patent Specification Nos. 1,515,604, 1,554,082 and 1,548,527, respectively, it is only possible for them to be subjected to hydropyrolysis provided that equilibrium establishment for the following reactions

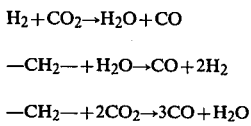

is avoided at the necessary temperature range of about 800° to 950° C. and also provided that neither the hydrocarbons nor carbon monoxide produce carbon black in quantities which are liable to adversely affect operation.

Unless catalytically promoted by contact of the reaction mixture with the wall of the pyrolysis reactor, the above reactions occur so reluctantly that they cannot reasonably be said to impair the yield of olefins formed by hydropyrolysis during the necessary short contact time of 0.02 to 2 seconds.

It has also been described that a quartz tube should conveniently be used for subjecting a gas mixture containing hydrocarbons, hydrogen, carbon monoxide, carbon dioxide and steam to hydropyrolysis therein. In a quartz tube, it has been possible to effect the reaction over a period of 250 hours substantially without undesirable disturbing deposition of carbon black. If carried out in a tube made up, e.g. of iron, temperature-resistant steels or nickel, the reaction just described is normally accompanied by undesirable formation of carbon black or decomposition of hydrocarbons.

The present invention relates more particularly to a process for the commercial production of ethylene by subjecting a gas mixture containing hydrocarbons, hydrogen, carbon monoxide, carbon dioxide and water to a pyrolysis reaction permitting the formation of carbon black (which may ultimately result in the tubular reactors becoming clogged therewith) and decomposition of hydrocarbons to be substantially avoided.

To this end, the invention provides for the gas mixture to be heated to temperatures higher than 800° C. inside a reaction zone having metal walls containing aluminum and/or copper in at least their surface portions facing and coming into contact with the gas mixture.

Preferred features of the present process provide:
(a) for the gas mixture to be heated to temperatures higher than 900° C.;
(b) for the gas mixture to be heated to temperatures up to 1000° C.;
(c) for the heated gas mixture to be maintained under a pressure of less than 5 bars;
(d) for the heated gas mixture to be maintained under a pressure within the range 1.5 to 4 bars;
(e) for the metal walls of the reaction zone to be made up of steel containing aluminum and/or copper;
(f) for the metal walls of the reaction zone to have aluminum and/or copper applied thereto;
(g) for the aluminum and/or copper to be applied to the metal walls via the gas phase with the use of one or more halogen compounds as transporting agent;
(h) for the aluminum and/or copper to be applied to the metal walls by contacting the latter with an aluminum and/or copper melt; and
(i) for the gas mixture to be used in further admixture with one or more gaseous sulfur compounds.

Materials which can be used for making the walls of the reaction zone comprise chrome and chrome-nickel steels which additionally contain aluminum, e.g. ALUCHROM (this is a registered Trade Mark; construction materials nos. 1.4765 and 1,4767 according to DIN-specification (DIN stands for German Industrial Standard) 17 470, July 1963); ARMCO 18 SR (this is a registered Trade Mark) or KANTHAL (this is a registered Trade Mark). In those cases in which steel substantially free from aluminum is used for making the walls of the reaction zone, it is necessary for aluminum to be applied to that side of the walls which faces and comes into contact with the gas mixture. Even aluminum-containing steel should have additional aluminum applied thereto as this permits the catalytic activity of the reactor walls to be further reduced.

One method of applying aluminum to the inside walls of a reaction zone comprises filling the zone with a mixture of pulverulent or granular aluminum and a porous carrier which does not react with aluminum, e.g. aluminum oxide, and annealing the mixture at 700° to 1000° C. under scavenging treatment with a mixture of nitrogen and aluminum chloride in vapor form. During that treatment which is effected over a period of 2 to 5 hours, it is possible for sufficient aluminum to diffuse into, and catalytically inactivate, the metal walls of the reaction zone.

Another method of applying aluminum to the inside walls of the reactor comprises filling the reactor with an aluminum melt of 700° to 900° C. and leaving the walls in contact therewith over 2 to 20 hours. Another method of reliably reducing the catalytic activity of metal walls comprises using the aluminum in further admixture with copper powder, copper granules or a copper melt, and contacting the metal walls therewith.

Still another method of reducing the catalytic activity of reactor inside walls comprises using the gas mixture in further admixture with one or more sulfur-containing compounds, e.g. $H_2S$, $CS_2$ and COS, and contacting the metal walls therewith.

EXAMPLES

In all of the following Examples, use was made of a gas mixture which was obtained by contacting a mixture of carbon monoxide and hydrogen which were used in a ratio by volume of 1:1, at 290° C. and under 16 bars with a carrier-supported catalyst containing iron, copper and potassium. The composition typical of the gas mixture is indicated in the following Table 1, left hand column.

The gas mixture used in each particular case was left uncooled and, after pressure release to 1 bar, it was introduced into a hydropyrolysis reactor of which the tubular structures which were heated over a length of 20 cm had an internal diameter of 10 mm. The various materials used for making the tubular structures are indicated in the following Table 2. The residence time of the gas mixture in the tubular structures was about 0.25 second, under the experimental conditions selected (1 bar; 890° C.). In Examples 13 to 22 listed in Table 2, the change in volume varied by about −10%.

As would appear to result from Table 2, comparative Examples 1 to 12, the tubular structures made from the materials specified were found to promote the formation of carbon black (which results in the tubular structures becoming ultimately clogged therewith) and/or to effect an increase in the CO-content and/or to produce reaction gas of low ethylene concentration.

This is in clear contrast with the results obtained with tubular structures made from materials in accordance with this invention (Examples 13 to 22). Reaction gas of high ethylene concentration was obtained. Even after prolonged operation, carbon black could not be found to have been formed. Nor could the CO-concentration be found to have been significantly increased, based on the CO-concentration of the feed gas mixture.

The analytical data typical of a gas obtained by the present hydropyrolysis process is indicated in Table 1, right hand portion.

In Table 2, the sign "a→b" indicates that the concentration in the hydropyrolysis gas changed from (a) to (b) volume % during the experiment.

TABLE 1

| | Gas mixture | | Hydropyrolysis gas | | |
|---|---|---|---|---|---|
| | Composition vol. % | Selectivity % | Composition vol. % | Yield %, based on CO reacted | C - % based on sum of hydrocarbons |
| $H_2O$ | 2.85 | | 2.79 | | |
| $O_2$ | 0.59 | | 0.48 | | |
| $N_2$ | 0.24 | | 0.24 | | |
| $H_2$ | 26.42 | | 29.62 | | |
| CO | 14.33 | | 13.48 | | |
| $CO_2$ | 34.32 | 46.51 | 31.34 | 47.12 | — |
| $CH_4$ | 12.80 | 17.35 | 12.89 | 19.48 | 36.84 |
| $C_2H_2$ | <0.01 | | 0.37 | 1.12 | 2.11 |
| $C_2H_4$ | 0.59 | 9.27 | 6.84 | 20.67 | 39.10 |
| $C_2H_6$ | 2.32 | | 0.53 | 1.60 | 3.03 |
| $C_3$ | 2.41 | 9.80 | 0.59 | 2.67 | 5.06 |
| $C_4$ | 2.35 | 12.74 | 0.12 | 0.37 | 1.37 |
| $C_5$ | 0.54 | 3.66 | 0.26 | | |
| $C_6$ | 0.15 | 1.22 | 0.09 | | |
| $C_7$ | 0.04 | 0.38 | 0.25 | 6.76 | 12.78 |
| $C_8$ | <0.02 | <0.22 | 0.07 | | |
| $C_{8+}$ | <0.02 | ~0.22 | ~0.04 | | |

TABLE 2

| | Material used for making tubular structure | Operation period (h) | CO-increase vol. % | content vol. % CH$_4$ | C$_2$H$_4$ | observations |
|---|---|---|---|---|---|---|
| | (Comparative Examples) | | | | | |
| 1 | Iron | 14 | 18 → 0 | 17 | 4.2 | clogged by |
| 2 | Iron, S-treated | 24 | 4 → 0 | 16 → 9 | 5.9 → 0.4 | carbon black |
| 3 | Iron, P-treated | 4 | 5 → 20 | 13 | 6 → 0.7 | |
| 4 | Iron, treated with silicic acid ester | 6 | 10 | 15 | 6 → 3.5 | |
| 5 | Iron, treated with silicic acid ester; annealed for 4 h | 18 | 16 → 2 | 11 → 8 | 2.8 → 0.4 | |
| 6 | Iron, treated with silicic acid ester; annealed for 4 h sulfided gas mixture | 3 | 5 → 15 | 12 → 17 | 5.5 → 18 | |
| 7 | Iron, gold-plated with H(AuCl$_4$) | 22 | 30 | 9 | 1.5 | |
| 8 | Steel; material no. 1.4016 (CEKAS; Reg. Trade Mark) | 19 | 3 | 12.8 | 5.9 | carbon black formation |
| 9 | Steel; material no. 1.4016 (CEKAS; Reg. Trade Mark); sulfided gas mixture | 21 | 1 | 15.2 | 6.0 | carbon black formation |
| 10 | Steel; material no. 1.4841 | 22 | 16 | 10.6 | 1.1 | |
| 11 | Steel; material no. 1.4541 | 12 | 18 | 12 | 4.2 → 2.0 | |
| 12 | Pure nickel, polished | 16 | 11 | 22.4 | 1.0 | carbon black formation |
| | (Examples in accordance with invention) | | | | | |
| 13 | ALUCHROM O | 250 | 0.5 | 16 | 6.2 | spontaneous |
| 14 | ALUCHROM O; sulfided gas mixture | 250 | 0 | 14.8 | 5.7 | ethylene drop after 89 h |
| 15 | ALUCHROM W | 92 | 0 | 14.6 | 7.1 | |
| 16 | KANTHAL DSD | 250 | 0 | 12.2 | 5.25 | |
| 17 | INCONEL 601; Al-plated | 250 | 1 | 16 | 6.9 | |
| 18 | ARMCO 18 SR | 250 | 2.6 | 16.8 | 6.6 | |
| 19 | ARMCO 18 SR; Al-plated | 250 | 1.5 | 16.8 | 7.2 | |
| 20 | Steel; material no. | 250 | 0 | 15.6 | 6.2 | |

TABLE 2-continued

| Material used for making tubular structure | Operation period (h) | CO-increase vol. % | content vol. % CH$_4$ | content vol. % C$_2$H$_4$ | observations |
|---|---|---|---|---|---|
| 1.4571 plated with Al and Cu | | | | | |
| 21 Steel; material no. 1.4571; Al-plated | 250 | 0 | 16.4 | 6.7 | |
| 22 Steel; material no. 1.4571; Cu-plated | 250 | −3.3 | 14.3 | 5.7 | |

We claim:

1. A process for making ethylene by subjecting a gas mixture containing hydrocarbons, hydrogen, carbon monoxide, carbon dioxide and steam to a hydropyrolysis reaction, which comprises heating the gas mixture to temperatures higher than 800° C. and maintaining the heated gas mixture under a pressure of less than 5 bars inside a reaction zone having metal walls made up of steel containing copper.

2. A process for making ethylene by subjecting a gas mixture containing hydrocarbons, hydrogen, carbon monoxide, carbon dioxide and steam to a hydropyrolysis reaction, which comprises heating the gas mixture to temperatures higher than 800° C. and maintaining the heated gas mixture under a pressure of less than 5 bars inside a reaction zone having metal walls coated with an overlayer of at least one metal selected from copper and aluminum, said overlayer being applied to the metal walls via the gas phase with the use of at least one halogen compound as a transporting agent.

3. The process as claimed in claim 1 or 2, wherein the gas mixture is heated to temperatures of 900°–1000° C.

4. The process as claimed in claim 1 or 2, wherein the heated gas mixture is maintained under a pressure of 1.5–4 bars.

5. The process as claimed in claim 1 or 2, wherein the gas mixture is used in further admixture with at least one gaseous sulfur compound.

* * * * *